(12) United States Patent
Lawler

(10) Patent No.: US 7,118,871 B2
(45) Date of Patent: Oct. 10, 2006

(54) REAGENTS FOR MONITORING NUCLEIC ACID AMPLIFICATION AND METHODS OF USING SAME

(76) Inventor: Joseph F. Lawler, 4125 Roland Ave., Baltimore, MD (US) 21211

(*) Notice: Subject to any disclaimer, the term of this patent is extended or adjusted under 35 U.S.C. 154(b) by 262 days.

(21) Appl. No.: 10/409,043

(22) Filed: Apr. 9, 2003

(65) Prior Publication Data

US 2004/0053287 A1   Mar. 18, 2004

Related U.S. Application Data

(60) Provisional application No. 60/374,479, filed on Apr. 22, 2002.

(51) Int. Cl.
    C12Q 1/68    (2006.01)
    C07H 19/04   (2006.01)
(52) U.S. Cl. ............... 435/6; 536/26.1; 536/26.6
(58) Field of Classification Search ............ 435/6; 536/26.1, 26.6
    See application file for complete search history.

(56) References Cited

U.S. PATENT DOCUMENTS

| | | | |
|---|---|---|---|
| 4,318,981 A | 3/1982 | Burd et al. | 435/7 |
| 5,047,519 A | 9/1991 | Hobbs, Jr. et al. | 536/23 |
| 5,622,821 A | 4/1997 | Selvin et al. | |
| 5,688,648 A | 11/1997 | Mathies et al. | |
| 5,723,591 A | 3/1998 | Livak et al. | |
| 6,037,130 A | 3/2000 | Tyagi et al. | |
| 6,228,994 B1 | 5/2001 | Yanagawa et al. | 530/402 |
| 6,232,075 B1* | 5/2001 | Williams | 435/6 |
| 6,306,607 B1 | 10/2001 | Williams et al. | |
| 2002/0115076 A1* | 8/2002 | Williams | 435/6 |

FOREIGN PATENT DOCUMENTS

| | | |
|---|---|---|
| WO | WO/9845309 | 10/1998 |
| WO | WO 00/36151 | 6/2000 |
| WO | WO/0036152 | 6/2000 |
| WO | WO/0148235 | 7/2001 |
| WO | WO/0286088 | 10/2002 |

OTHER PUBLICATIONS

A. A. Arzumanov, D. G. Semizarov, L. S. Victorova, N. B. Dyatkina, A. A. Krayevsky, *J Biol Chem* 271, 24389-94 (Oct. 4, 1996).
G. Benga, S. J. Strach, *Biochim Biophys Acta* 400, 69-79 (Jul. 21, 1975). [Abstract only].
J. Compton, *Nature* 350, 91-2 (Mar 7, 1991). [Abstract only].
Glonek et al., *Science*, 185, 352-355 (Jul. 1974).
M. E. Gorre et al., *Science* 293, 876-80 (Aug. 3, 2001).
I. V. Kutyavin et al., *Nucleic Acids Res* 28, 655-61 (Jan. 15, 2000).
P. M. Lizardi et al., *Nat Genet* 19, 225-32 (Jul. 1998).
V. Lyamichev, M. A. Brow, J. E. Dahlberg, *Science* 260, 778-83 (May 7, 1993).
K. Nath, J. W. Sarosy, J. Hahn, C. J. Di Como, *J. Biochem Biophys Methods* 42, 15-29 (Jan. 3, 2000).
N. P. Shah et al., *Cancer Cell* 2, 117-25 (Aug, 2002).
H. Weizman, Y. Tor, *J Am Chem Soc* 124, 1568-9 (Feb. 27, 2002).
P. Wu, L. Brand, *Anal Biochem* 218, 1-13 (Apr. 1994). [Abstract only].

* cited by examiner

*Primary Examiner*—Johann Richter
*Assistant Examiner*—David P. Stitzel
(74) *Attorney, Agent, or Firm*—Chalin A. Smith; Smith Patent Consulting

(57) ABSTRACT

Described herein are novel indicator molecules of general formula (1):

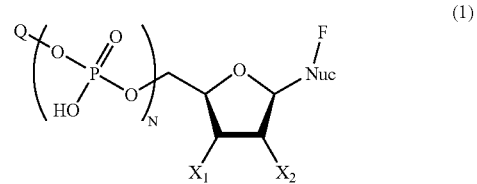

wherein Q, F, N, Nuc, $X_1$ and $X_2$ are as defined herein, including their tautomeric forms and their additive salts. The present invention also concerns methods for the use of these molecules to monitor nucleic acid amplification in real time and their applications as diagnostics.

24 Claims, 6 Drawing Sheets

REAGENTS FOR MONITORING NUCLEIC ACID AMPLIFICATION AND METHODS OF USING SAME

PRIORITY INFORMATION

This application claims the benefit of U.S. Provisional Application Ser. No. 60/374,479, filed Apr. 22, 2002, which is incorporated by reference herein in its entirety.

TECHNICAL FIELD OF THE INVENTION

This present invention relates to reagents for monitoring nucleic acid amplification. More particularly, the present invention provides labeled nucleotide molecules that may be used to monitor nucleic acid amplification reactions, such as PCR, in real time.

BACKGROUND OF THE INVENTION

Normal cells must coordinate the activities of a number of cellular processes and pathways. One of the most important mechanisms by which this is accomplished is transcriptional regulation. Microarray hybridization experiments have identified many transcripts that are dysregulated in response to a given challenge or disease (1, 2). The identity of these dysregulated transcripts often permits an insight into the molecular nature of the process in question. These transcripts may also serve as important diagnostic and/or prognostic markers.

Once specific disease markers have been identified, it is important to develop rapid and reliable tests for detecting them. The applications for such tests are wide ranging. They can be used in clinical laboratories, to guide treatment decisions, or they can be used remotely, for the rapid detection of biological weapon dissemination. Real-time PCR is a method ideally suited for this purpose because of its exquisite sensitivity and speed. However, while there are a number of methods for quantifying PCR in real-time, each suffers from limitations.

In the past, transcript quantification was accomplished with northern blots, which are time consuming and typically rely on radio-isotopic methods of detection. Northern blots provide information on the length of a mRNA as well as its abundance but are generally limited to the study of 1 or 2 different mRNAs. Dot blots allow slightly more mRNAs to be analyzed but do not provide any information about transcript length or integrity.

One problem associated with preparing probes for Northern, Southern and dot blot analysis is that the failure to remove unincorporated label can result in unacceptably high background signals. Labels can be removed via any one of a number of approaches but this is an extra step requiring fluid handling steps that are difficult to automate.

The more recently developed microarray technologies allow one to quantify thousands of different RNA species in parallel. One limitation of microarrays is that only 1 or 2 different samples may be analyzed per array. This limitation results from the number of compatible fluorescent labels that may be used in a single hybridization experiment and the hybridization characteristics of the features on the array.

The number of samples that can be processed for microarray analysis in a given amount of time is also limited. The sample must be denatured to allow primers to anneal and a reverse transcriptase must be added to synthesize cDNA. The sample must be reverse transcribed in the presence of a fluorescently-labeled deoxynucleobase triphosphate so that it can be visualized on the array. Prior to applying the cDNA to the array however, unincorporated fluorescent nucleotides must be removed from the sample. This process involves multiple fluid handling steps, is difficult to automate, and adds significantly to the cost of an experiment. These difficulties are not unique to microarray experiments as any hybridization based detection method requires the separation of unincorporated label prior to applying a hybridization probe. Failure to do so often results in unacceptable background signal.

Ideally, one would like to increase the power of transcript analysis by analyzing thousands of mRNAs in thousands of different samples. This can be accomplished by increasing the throughput of microarfay experiments or by extending real-time PCR techniques to permit the analysis of more transcripts in parallel. Real-time PCR is an attractive alternative to microarrays as it can be used to analyze a few genes in a large number of samples. However, quantifying PCR in real-time is challenging, expensive, and limited to a few genes at a time.

Currently, there are three major types of "probes" used for quantifying PCR in real-time. They include double stranded DNA (dsDNA) binding dyes, such as ethidium bromide (EtBr) (3); the Taqman™ probe (see U.S. Pat. No. 5,723,591); and molecular beacons™ such as described in U.S. Pat. No 6,037,130. While each have certain advantages, none are ideally suited for monitoring the progress of many nucleic acid amplification reactions in real-time. For example, dsDNA binding dyes enjoy a substantial increase in fluorescence upon binding to dsDNA and can be included in a PCR to monitor the appearance of dsDNA, presumably due to PCR amplification. Their popularity results from their ease of use in that no probe design or oligonucleotide synthesis is necessary. However, these dyes cannot distinguish amplicon dsDNA from template dsDNA. Although this is not a problem when minute amounts of template are used, it can become a problem when complex template preparations, such as cellular DNA and whole blood, are used or when considerable amounts of template DNA are required (e.g., allele specific PCR (3, 4)). If 500,000 cells served as the starting material (as might be required for the detection of rare polymorphisms) then there would be micrograms of DNA template in the PCR. dsDNA binding dyes will generate a strong signal in the presence of this amount of template DNA, irrespective of the progress of the PCR. Accordingly, they cannot be used to monitor the progress of the PCR reaction.

dsDNA binding dyes bind to DNA non-specifically; thus, no nucleotide specificity is obtained. One must perform a melting curve after the amplification reaction to verify that the amplicon has the expected melting temperature. In practice, the melting curve requirement adds time to the procedure and limits amplicon size to approximately 300 bp. Linearity of the fluorescence signal becomes compromised when amplicons greater than 300 bp are studied. Furthermore, temperatures that denature DNA are encountered during each cycle of the PCR. During the time that the DNA is denatured, no signal can be measured using dsDNA binding dyes. This restricts fluorescence measurements to a period of time when the temperature of the reaction mixture is less than the melting temperature of the amplicon of interest.

Moreover, since these dyes must be present at a significant concentration in the amplification reaction, they add to its cost. High concentrations of dye may also impair polymerase fidelity and processivity (5). Finally, because they are mutagenic, the cloned products of a PCR monitored with these dyes may not be faithful copies of the starting material.

The Taqman™ probe is a short oligonucleotide that contains a fluorophore and a quencher. The fluorophore emission is mitigated by the quencher via energy transfer. During PCR, the probe anneals to the amplicon and is hydrolyzed by the 5' to 3' exonuclease activity of the polymerase. An increase in fluorescence signal is inferred to be due to an increase in the amount of amplicon present.

Fluorescence resonance energy transfer (FRET) efficiency decreases with the inverse sixth power of the distance between the reporter and the quencher. In practice, this limits the distance between the reporter and the quencher to less than 70 Angstroms (Å). This is a serious drawback of the Taqman™ assay. On one hand one wishes to design a longer probe to enhance hybridization specificity. However, a long probe will not permit efficient quenching of the reporter molecule by the quencher. Derivatizing the oligonucleotides with minor groove binding antibiotics improves its hybridization properties without increasing probe lengths (6). However, such modifications are expensive and requires special synthetic techniques.

Additional constraints on Taqman™ probe design exist and are problematic. For example, the probes must contain a modified nucleotide at their 3' terminus to prevent extension by the polymerase. Taqman™ probes also cannot have a guanosine residue at their 5' terminus or the fluorophore will be excessively quenched even after the oligonucleotide has been hydrolyzed. Homopolymeric runs of greater than four guanosines in a row are also not allowed and no more than 2 of the final 5 bases may be guanosine.

Furthermore, to be compatible with Taqman™ probes, the DNA polymerase used in the amplification reaction must have a 5' to 3' exonuclease activity (7). Thermophilic DNA polymerases commonly used for PCR including Vent™, Pfu™, and Tfu™ lack this activity and are therefore incompatible with the use of Taqman™ probes. This is problematic because, unlike Taq, these polymerases have the desirable property of high fidelity amplification. Thus far, only Taq DNA polymerase has been used successfully with Taqman™ probes.

Finally, Taqman™ probes require thermal denaturation in order to detect an amplicon, and are not capable of monitoring isothermal amplification methods such as Rolling Circle Amplification (RCA), Nucleic Acid Sequence Based Amplification (NASBA) and 3SR (8–10). The products of the detection process, fluorescent nucleobase monophosphates, can diffuse from their site of synthesis and as such, the Taqman™ assay is unsuitable for in situ applications.

Regarding, molecular beacons™, such as those described in U.S. Pat. No. 6,037,130, like the Taqman™ probe, they also consists of an oligonucleotide derivatized with a fluorophore and a quencher. The molecular beacon™ probe has internal complementarity and forms a stem loop in the absence of a target sequence. Stem loop formation brings the fluorophore and quencher into proximity and reduces the fluorescence emission. In a PCR, the molecular beacon™ hybridizes to an amplicon and its fluorescence emission increases.

However, molecular beacons™ also have a number of problems associated with them, many of which are similar to those described above in connection with the Taqman™ probes. Like Taqman™ probes, the design of molecular beacon™ oligonucleotide probes remains challenging. They must have a region of internal complementarity that is stable enough to remain in a stem loop in the absence of an amplicon but not so stable that its hybridization to the amplicon is compromised. Efforts to increase the hybridization efficiency by increasing the concentration of molecular beacon™ probe will result in decreased amplification efficiency, since the DNA polymerase must displace hybridized beacons™ during the reaction which decreases the rate of polymerization (an excess of probe also increases background fluorescence). Only a few thermophilic DNA polymerases possess the strand displacement activity required to displace a hybridized molecular beacon™.

Furthermore, as the reaction temperature rises during the PCR, molecular beacon™ probes denature and the observed fluorescent signal increases independent of the progress of the amplification reaction. Like dsDNA binding dyes, this restricts fluorescence measurements to a period of time when the temperature of the reaction mixture is less than that of the molecularbeacon™ probe.

Finally, the hybridization of either a Taqman™ or molecular beacon™ oligonucleotide probe to the target amplicon is quite sensitive to the primary sequence of the amplicon. As a result, innocent polymorphisms near the region being interrogated by the probe can render the probe completely ineffective as a reporter of amplicon concentration. While dsDNA binding dyes do not suffer from this limitation, they are incompatible with the complex templates commonly encountered in clinical and research labs. The molecules of the present invention are the only type of real-time PCR probe that can overcome this problem.

Thus, there is a clear need for a reagent that not only addresses the above-noted problems but combines the sensitivity of oligonucleotide probes with the convenience of dsDNA binding dyes. This need will become increasingly apparent as more ambitious expression profiling projects are undertaken. For example, there is currently great interest in performing thousands of PCRs in parallel in small, isolated chambers. One might want to rapidly analyze transcript levels in a very small amount of a particular tissue source. This type of approach, in which several dozen genes are analyzed simultaneously, has shown great promise in the early detection of biological weapon exposure (11). While the instrumentation for performing thousands of PCRs in parallel exists, there are considerable problems associated with monitoring these reactions simultaneously. Also, baseline expression levels of the genes of interest can vary greatly, as can the window in which real-time quantification will be in the linear range.

A large scale, real-time PCR approach necessitates that each chamber receive an equal amount of template. This amount must be sufficiently large for rare transcripts to be represented. However, this poses a problem for the use of dsDNA binding dyes as probes of these reactions since they will non specifically bind to the template and generate a background signal. This problem is exaggerated when a rare transcript is analyzed because more template is required. Taqman™ probes and molecular beacons™ are also not acceptable for a large scale, real-time PCR based approach for a number of reasons, not the least of which is cost. Probe design for both is problematic and this experiment potentially requires thousands of quality controlled oligonucleotide probes. Even if probes could be successfully designed with 90% efficiency, there would still be hundreds of probes requiring re-design and re-synthesis.

With respect to biological weapon (BW) detection, it is essential that any detection method used be robust enough to detect those agents that have been designed precisely to make detection more difficult. For example, if a weapons producer knew the sequence of the Taqman™ or molecular beacon probe being used for detection, it would be trivial to modify the sequence of the BW agent such that it is no longer detectable. This leads to an ever escalating process of BW agent modification to avoid detection and new probe design and synthesis to detect the modified agent. The ultimate outcome of this process is that one must perform a test with hundreds and possibly thousands of probe combinations to be assured that a modified agent has not been used. This is especially problematic when purified template is in limiting supply, as it so often is.

Thus, while it is clear that various real-time approaches to expression profiling will be used in the future, it is equally clear that the existing methods of quantification are inadequate for the experiments currently under consideration. Each of the approaches to cDNA labeling and real-time PCR analysis described herein, while solving some of the problems associated with traditional methods, introduces several problems of its own. In general, most of these methods are expensive, require extensive sample preparation, and require extensive fluid handling steps to separate incorporated from unincorporated labels. Therefore, new methods of quantification that do not suffer from these limitations are needed.

In sum, a need currently exists for sensitive and inexpensive methods for labeling nucleic acids that 1) do not require the separation of unincorporated label prior to downstream applications, 2) can be used to monitor nucleic acid amplification in real-time and 3) can be used to detect the presence of a polymerase. The present invention provides a method and reagents for accomplishing these and other goals.

SUMMARY OF THE INVENTION

Accordingly, the present invention provides novel indicator molecules of general formula (1) shown below:

$$\text{(1)}$$

$$Q-\left(\begin{array}{c}\text{O}\\\|\\\text{P}\\|\\\text{HO}\end{array}-\text{O}\right)_N-\text{O}-\begin{array}{c}\text{O}\\ \diagup\diagdown\\ X_1\quad X_2\end{array}-\text{Nuc}-F$$

wherein:
  Nuc represents a nucleobase selected from the group consisting of adenine, cytosine, guanine, thymidine, uracil and analogs thereof;
  N represents a number from 1 through 8 indicating the number of phosphate moieties present in said molecule;
  $X_1$ and $X_2$ are independently selected from the group H, OH, $NH_2$, O-alkyl, N-alkyl, S-Alkyl, P-alkyl, a halogen, an alkyl, a cyclo-alkyl, and an aromatic containing group, wherein the alkyl and cycloalkyl possess varying degrees of unsaturation and are optionally substituted; and
  F and Q comprise a pair of indicators, wherein cleavage of the molecule results in separation of the indicators which, in turn, yields a change in a measurable signal.

The measurable signal to be detected varies with the selection of F and Q. In a preferred embodiment, F and Q are independently selected from the group consisting of: fluorophores, quenchers, shift reagents, spin labels, radioisotopes, and magnetic resonance contrast agents. Likewise, the measurable signal is preferably selected from fluorescence, magnetic field (magnetic resonance), and radiation intensity.

In one preferred embodiment, F and Q comprise a fluorophore and a quenching moiety and the change in measurable signal is selected from a change in fluorescence intensity, lifetime or polarization. It is preferred that F not be a quencher of Q's fluorescence.

In a further preferred embodiment, F is bound to Nuc directly or via a cleavable linker. Alternatively, F and Nuc can cyclize to form an intrinsically fluorescent nucleobase analog.

The molecules of the present invention provide a number of advantages and address a number of deficiencies associated with existing methods. For example, the molecules of the present invention eliminate or minimize background noise, in that they are preferably "dark" until cleaved by a polymerase, at which point the Nuc-F moiety emits a measurable signal, such as change in fluorescence intensity, lifetime or polarization or change in electron paramagnetic resonance.

Furthermore, unlike dsDNA binding dyes, the molecules of the present invention demonstrate some sequence specificity as a function of their nucleobase moiety. Unlike, dsDNA binding dyes, which may incorporate anywhere along the double helix, the molecules of the present invention will only label the DNA strand at positions in which its nucleobase can base pair with the template strand.

The molecules of the present invention are especially sensitive for real-time PCR for two reasons. First, unlike Taqman™ and molecular beacon™ probes, more than one indicator molecule is generated per amplicon. The "label" generated by the molecules of the present invention is covalently bound to the DNA into which it incorporated, thereby obviating the need for the label to "re-bind" to the amplicon each cycle. Thus, PCR monitoring in real time is not restricted to temperatures below the melting temperature of the amplicon. Second, the molecules of the present invention also independently generate a signal for each strand of the amplicon whereas dsDNA binding dyes require both strands of DNA to be present and annealed to generate a signal.

Another advantage of the indicator molecules of the present invention is that they allow for considerable flexibility in the choice of label used as the reporter. dsDNA binding dyes are designed to fluoresce only when bound to dsDNA. This imposes severe structural constraints on these molecules and limits the optimization of optical parameters, such as quantum yield and emission maxima. The molecules of the present invention have no such "functional" constraints. They need only be tolerated by a DNA polymerase. Further, the molecules of the present invention are not known mutagens.

The molecules of the present invention are also advantageous in that complex oligonucleotide probe design is not required. Accordingly, they are not susceptible to the "masking" techniques described above. As long as a target agent can be amplified with some type of nucleic acid amplification procedure, the molecules of the present invention can be used to detect it and can do so in the context of a heterogeneous template preparation. Finally, the molecules of the present invention are also compatible with ambient isothermal amplification protocols.

The present invention further provides methods for preparing the inventive molecules and methods and assays using the inventive molecules to monitor nucleic acid amplification and polymerase activity in real-time.

Accordingly, it is an object of the present invention to provide method for monitoring the progress of a nucleic acid amplification reaction, including but not limited to PCR, RCA, NASBA, and 3SR, in real time. Specifically, the present invention provides a method of detecting nucleic acid amplification comprising the steps of: (a) contacting a polymerase with a primer, a template, nucleobase triphosphates and one or more molecules of the formula (1) in a medium in which the polymerase is active; and (b) detecting a change a measurable signal.

In one embodiment of this invention, nucleic acid labeling is effected by contacting a primer, a template, deoxynucleobase triphosphates, a polymerase, and the inventive indicator molecules under conditions in which DNA synthesis is promoted. The inventive molecules are essentially "dark" (i.e., emit essentially no signal) until such time as they are incorporated by said polymerase. Incorporation involves cleavage of molecule, which, in turn, liberates the Q-pyrophosphate moiety from the parent molecule. Separation of F and Q results in a change in measurable signal, such as a change in fluorescence intensity, lifetime or polarization or electron paramagnetic resonance. Accordingly, cleavage of the parent molecule increases the quantum yield of F, which is now part of a larger nucleic acid molecule. The labeled probe can be directly used in an application without subsequent purification because un-incorporated molecules of the present invention are "dark" and as such will not contribute significantly to a background signal.

In another embodiment of this invention, a nucleic acid amplification reaction is monitored in real-time by adding a molecule of the present invention to the reaction. The nucleic acid amplification reaction is assembled as usual, with the exception that molecules of the present invention are present. Importantly, the molecules of the present invention may comprise part of a homogeneous or heterogeneous assay. The methods and reagents described herein make no distinction between heterogeneous and homogeneous assays. The molecules described herein can be adapted to either purpose. For either type of assay, as the amplification reaction proceeds, the inventive molecules are incorporated by the polymerase as discussed above. A resulting change in a measurable parameter can be monitored to follow the progress of the reaction.

It is yet another object of the present invention to provide a method for determining the presence and amount of a hydrolyzing enzyme in a sample. For example, in one embodiment, the present invention provides a method for detecting the presence of active polymerase in a medium comprising the steps of: (a) contacting a polymerase with a primer, a template, nucleobase triphosphates and one or more molecules of the formula (1) in a medium in which the polymerase is active; and (b) detecting a change a measurable signal. The polymerase may comprise a DNA polymerase, an RNA polymerase or a reverse transcriptase. Likewise, the medium may be a body fluid selected from blood, plasma, serum, CSF, urine, semen, tears, saliva, bile, gastric secretions and breast milk.

In a preferred embodiment of this invention, the presence of a polymerase in a sample is detected by supplying a primer, a template, deoxynucleobase triphosphates, and the molecules of the present invention under conditions in which nucleic acid synthesis is promoted. The extent to which molecules of the present invention are incorporated by the polymerase can be determined by monitoring the resulting increase in measurable signal, such as fluorescence or electromagnetic emission. The degree of signal detected correlates to the amount of polymerase present in said sample. As discussed above, incorporation liberates a Q-pyrophosphate moiety from the parent molecule. This increases the quantum yield of F, which is now part of a larger nucleic acid molecule. The labeled probe can be directly used in an application without subsequent purification because un-incorporated molecules of the present invention are "dark" and as such will not contribute significantly to a background signal.

It is a further object of present invention to provide an assay for detecting the presence of an active viral polymerase in a sample. In addition to one or more molecules of formula (1), the assay preferably includes a polymerase with a primer, a template, nucleobase triphosphates. The assay finds particular utility as an HIV assay, detecting the presence of active HIV reverse transcriptase in a body fluid such as blood, plasma, serum, CSF, urine, semen, tears, saliva, bile, gastric secretions or breast milk.

In yet another embodiment of this invention, the presence of a phosphodiesterase may be detected by molecules of the present invention under conditions in which said phosphodiesterase is enzymatically active. Specifically, the present invention provides a method of detecting a phosphodiesterase comprising the steps of: (a) contacting one and one or more molecules of the formula (1) with a phosphodiesterase in a medium in which the phosphodiesterase is enzymatically active; and (b) detecting a change in said measurable signal.

In still another embodiment of this invention, the presence of a cyclase in a sample may be detected by molecules of the present invention under conditions in which said cyclase is enzymatically active. Specifically, the present invention provides a method of detecting nucleobase cyclase activity comprising the steps of: (a) contacting one or more molecules of the formula (1) with a cyclase in a medium in which the cyclase is enzymatically active; and (b) detecting a change in said measurable signal. The extent to which molecules of present invention are utilized by said cyclase can be determined by monitoring the resulting change in measurable signal, arising from the separation of F and Q. The amount of signal detected serves as a surrogate for the amount of cyclase present in said sample.

These and other objects and features of the invention will become more fully apparent when the following detailed description is read in conjunction with the accompanying figures and examples.

DETAILED DESCRIPTION OF THE INVENTION

Figure 1:
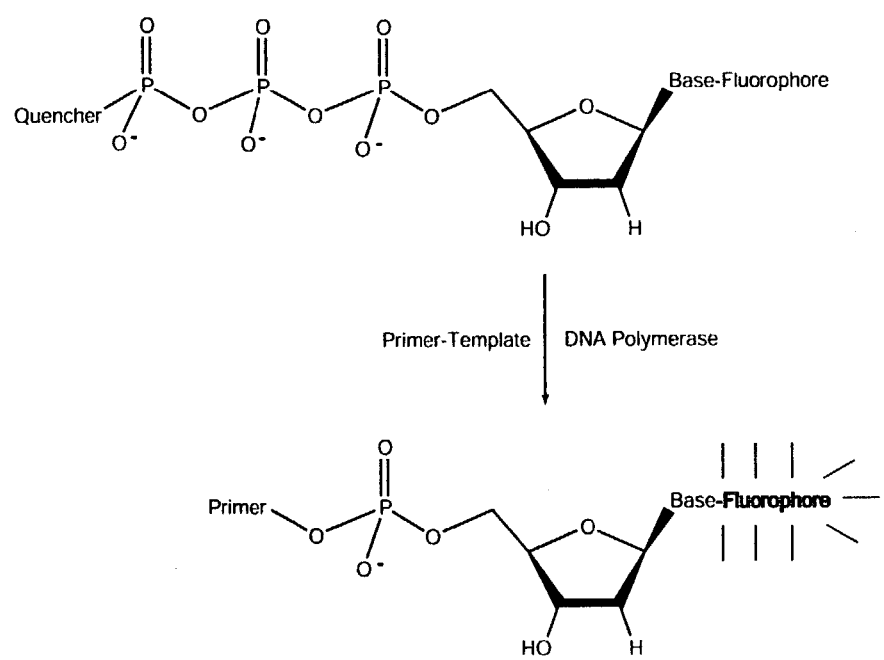
FIG. 1 contains a schematic representation of how the molecules of the present invention generate a detectable fluorescence signal.

As noted above, a need currently exists for sensitive and inexpensive methods for labeling nucleic acids that 1) do not require the separation of unincorporated label prior to downstream applications, 2) can be used to monitor nucleic acid amplification in real-time and 3) can be used to detect the presence of a polymerase. The present invention provides a method and reagents for accomplishing these and other goals.

The molecules of the present invention are represented by formula (1) shown below:

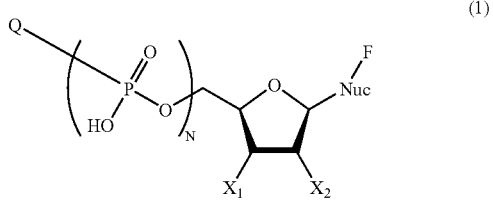

(1)

and include additive salts and tautomeric forms thereof.

In the context of the present invention, the following definitions apply:

F and Q of formula (1) comprise a pair of indicators, wherein cleavage of the molecule results in separation of the indicators which, in turn, yields a change in a measurable signal. In the context of the methods of the present invention, this cleavage arises from contact with an enzyme that hydrolyzes the molecule. Examples of such enzymes include, but are not limited to, polymnerases, cyclases, and phosphohydrolyases. Examples of polymerases useful in the context of the present invention, include, but are not limited to, DNA polymerase, RNA polymerase and reverse transcriptase.

In the context of the present invention, F and Q may comprise paired fluorophores and quenchers, spin labels, radioisotopes, and magnetic resonance contrast agents. The measurable signal may comprise any detectable parameter that may be measured using conventional equipment; however, the detectable signal to be measured varies with the selection of indicators. Examples include, but are not limited to, fluorescence emission, intensity, lifetime and polarization; magnetic field, radiation intensity, and the like. The signal may comprise any In one embodiment, F and Q comprise a fluorophore and quencher, respectively. There are a large number of fluorophores that could potentially be selected to occupy the position entitled "F" in the molecule of the present invention. There are a number of fluorescent molecules known to those of reasonable skill in the art. The choice of fluorophore is dictated by a number of factors including whether its presence is compatible with successful incorporation of the molecule by a polymerase. Other factors include emission wavelength, quantum yield and whether or not its presence substantially alters the molecule's solubility or stability. In multiplexing situations, it is important to select fluorophores whose emissions can be spectrally resolved. In other instances, it might be desirable for the fluorophore to function as a label of identity wherein the identity of the nucleobase can be determined by the nature of the fluorescent label. Such labels of identity will find utility in single base extension reactions, DNA sequencing, and single nucleotide polymorphism (SNP) genotyping.

It may also be desirable to select F and Q to be a pair of fluorophores. It is preferred that F not be a quencher of Q's fluorescence as a goal of the present invention is to allow the nucleic acid amplicon to emit a detectable signal upon incorporation of the parent molecule by the polymerase. In this context, the donor fluorophore or quencher can absorb light and transmit the energy to the acceptor fluorophore. If the quencher is present, the acceptor fluorophore emission will not be detected however, upon incorporation the quencher will be liberated and the emission will be detectable.

The quenching moiety present on the molecules of the current invention may be "dark" quenchers in that they quench the emission of the fluorophore and do not emit light themselves or they may be a second fluorescent molecule that quenches the emission of the fluorophore and emits light at a different wavelength. The principle in which a fluorophore is quenched by a second fluorophore which then emits light is known as fluorescence resonance energy transfer of FRET. An advantage inherent in the use of using a quenching moiety that emits light in response to FRET is that one may monitor an increase in donor emission or a decrease in acceptor emission. A second advantage is that it is sometimes possible to monitor fluorescence emission polarization which is a parameter that is independent of fluorescence intensity.

Fluorescence quenching via Fluorescence Resonance Energy Transfer of FRET is a physical phenomenon in which the energy of an excited state fluorophore (the donor) is non-radiatively transferred to a second molecule (the acceptor) (12). In addition to its sensitivity on spectral overlap between the donor emission and the acceptor absorption, FRET is also exquisitively dependent on the distance between the donor and acceptor. FRET efficiency decreases with the inverse sixth power ($r^{-6}$) of the distance between donor and acceptor. Therefore, a requirement for efficient FRET is that the donor and acceptor be in close proximity. This condition is satisfied by the molecules of the preferred invention.

The advantage conferred with a two fluorophore system is that a single donor fluorophore can be used in conjunction with multiple acceptor fluorophores. This can simplify instrumentation as only a single excitation wavelength is required to elicit multiple, spectrally distinct emissions. Such fluorophore pairs are the subject of U.S. Pat. No. 5,688,648, the contents of which are incorporated by reference herein.

In certain instances, the F component of the molecule may comprise a more than one fluorophores, e.g., $F_1$ and $F_2$. For example, in the embodiment wherein the nucleobase is adenine, the two fluore system may comprise fluorescein and rhodamine in combination with Q component comprising a broad spectrum quencher such as Dabsyl. Alternatively, in the embodiment wherein the nucleobase is thymidine, $F_1$ and $F_2$ may comprise fluorescein and Texas Red, respectively, and Q again may comprise a broad spectrum quencher such as Dabsyl. Fluorescein serves as a FRET donor to both Rhodamine and Texas Red; therefore, a single light source may be used to interrogate either molecule. This obviates the need for separate light sources and/or filters and can simplify the instrumentation used to analyze the progress of nucleotide incorporation. Examples of suitable fluorophores include, but are not limited to, optionally substituted pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benz-phenalenones, carbazines, oxazines, 4-bora-3a,4a-diaza-s- indacenes, fluorophoresceins, rhodamines, rhodols, 5-carboxyfluorophoresceins (FAM), 5-(2'-aminoethyl)aminonapthalene-1-sulfonic acids (EDANS), anthranilamides, terbium chelates, Reactive Red 4, Texas reds, and BODIPY dyes.

Examples of suitable quenchers include, but are not limited to, optionally substituted phenyls, naphthyls, anthracenyls, benzothiazoles, benzoxazoles, or benzimidazoles, pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins (FAM), 5-(2'-aminoethyl)aminonapthalene-1-sulfonic acids (EDANS), anthranilamides, terbium chelates, Reactive Red 4, dabcyls, nitrotyrosines, malachite greens, Texas reds, dinitrobenzenes, and BODIPY dyes Proximity based detection methods are not limited to fluorescence although fluorescent methods currently enjoy wide usage. The molecules of the present invention could readily be modified to include labels containing unpaired electrons in the place of the fluorophore and quencher. Such labels, known to those skilled in the art, can be detected by electron spin resonance (ESR) and other techniques. Established synthetic routes by which they can be coupled to molecules of interest are also well known (13). Accordingly, in an alternate preferred embodiment, F and Q comprise paired ESR labels or "spin labels". When spin labels are brought into proximity with each other, spectral changes can be observed. Polymerase utilization of the molecule of the present invention, modified to harbor spin labels in the place of the fluorophore and quenching moiety, could be detected by electron spin resonance or some other suitable spectroscopic technique.

Lanthanide elements are well know to those of reasonable skill in the art as "shift reagents". These elements can be used to alter the relaxation properties of adjacent nuclei. This change in relaxation is detectable by nuclear magnetic resonance spectroscopy (NMR). Molecules of the present invention, wherein a shift reagent is present at the F position which alters the relaxation of a nuclei present at or near the Q position, can be used to monitor the progress of a nucleic acid amplification reaction by NMR.

In another preferred embodiment, F and Q comprise a radio-isotope label and fluorophore. In this context, the fluorophore absorbs radiation from the radio-isotope and emits at a different wavelength. The efficiency of this process is governed by, among other things, proximity. Separation of the fluorophore and the radio-isotope can be monitored by a change in fluorescence intensity.

The Nuc moiety shown in formula (1) represents a purine or pyrimidine nucleobase, such as adenine, cytosine, guanine, thymidine, or uracil or analogs thereof. F may be directly attached to Nuc or may be attached via a cleavable linker. Nucleotides with dozens of different labels tethered to the nitrogenous base have been incorporated into DNA by polymerases. There is a tremendous amount of flexibility with respect to the type of fluorescent base modifications that are tolerated by polymerases. A representative sampling of these modifications includes dozens of fluorophores, biotin, haptens and heterobinuclear metal clusters. The molecular weight of this last modification exceeds 1,000 grams per mole (14). This flexibility coupled with broad spectrum quenchers will permit the synthesis of the molecules of the present invention with virtually any fluorescent label one wants. Certain metal chelates have the advantage of exceptionally long emission lifetimes and are able to participate in FRET with other fluorophores and quenching moieties U.S. Pat. No. 5,622,821.

Alternatively, F and Nuc may together form a multicyclic ring that is intrinsically fluorescent. Intrinsically fluorescent nucleotide analogs that correctly base pair are described in the literature (15, 16). If a fluorescent nucleotide analog is used, then an additional fluorophore need not be attached to said nucleotide analog. In this embodiment, the emission of the fluorescent nucleotide analog is quenched until such time as it is incorporated by a polymerase. Fluorescent nucleotide analogs are smaller than the corresponding natural nucleobase and attached fluorophore. This attribute may be advantageous when assaying a polymerase that fails to incorporate nucleobases with attached fluorophores. Intrinsically fluorescent nucleobase analogs may also exhibit environmentally sensitive fluorescence which could be used to further characterize the products of a polymerization reaction. In general, it is desirable to use an intrinscally fluorescent nucleotide that is excited by electromagnetic radiation of a wavelength that is not also absorbed by the natural nucleobases.

A number of modified nucleobases have been described in the literature and are known to those of ordinary skill in the art. The selection of a nucleobase analog is guided by the application in which it may possess a particular advantage over the corresponding nucleotide. For example, guanine derivatives have long been used in DNA sequencing reactions to alleviate band compression artifacts. Not all modified nucleobases are capable of being incorporated by a polymerase. However, any nucleobase analog that is incorporable by a polymerase may be used in the context of this invention. Examples of suitable nucleobase analogs include, but are not limited to, deazoapurines and intrinsically fluorescent moities, such as cytidine, nicotinamide adenosine, and 2-aminopurine, 2-thiopyrimidine poly(1, N6-ethenoadenylic acid) 2-thiouridylic acid) and poly(2,4-dithiouridylic acid) and the like (14, 15).

As shown in formula (1), the nucleobase is linked to a sugar, typically a pentose, at the 1' position. The Nuc-sugar moiety is referred to herein as a "nucleoside". Nucleosides suitable for use in the present invention include, but are not limited to, synthetic nucleosides having modified base moities (e.g., nucleobase analogs) and/or modified sugar moieties. The sugar component of the nucleoside may be selected from the group consisting of riboses, deoxyriboses, acyclics, carbocyclics, dideoxyriboses, hexoses, and dideoxydidehydroriboses. The pentose is optionally substituted at the 2' and/or 3' positions with $X_1$ and $X_2$, wherein $X_1$ and $X_2$ are selected from the group H, OH, $NH_2$, $N_3$, O-alkyl, N-alkyl, S-Alkyl, P-alkyl, a halogen, an alkyl, a cycloalkyl, O-cycloalkyl, N-cycloalkyl, S-cycloalkyl, P-cycloalkyl, aryl, O-aryl, N-aryl, S-Aryl, P-aryl.

Nucleobases modified at the sugar moiety can have profound effects upon incorporation into a DNA strand. For example, the dideoxynucleobase triphosphates used in Sanger's method of DNA sequencing effect chain termination upon incorporation. The nucleobases of the present invention could also incorporate sugar modifications. The nature of the modification will be dependent on the application. Modifications to the sugar moiety may effect chain termination (e.g, dideoxynucleotides) or may permit subsequent chain cleavage (e.g., ribonucleotides).

The molecules of the current invention may possess a variable number phosphate groups. The number of phosphates moieties present in the molecule is designated by the letter N of formula (1), which may range from 1 through 6. The Nuc-pentose-phosphate moiety is referred to herein as a "nucleotide". The term "nucleotide" as used herein refers to the phosphate ester of the nucleoside, typically mono-, di- and triphosphate esters, wherein the most common site of esterification is the hydroxyl group attached to the C-5 of a pentose. Suitable nucleotide triphophates (or NTPs) useful in the context of the present invention include, but are not limited to, ATP, dATP, CTP, dCTP, GTP, dGTP, TTP, dTTP, UTP, and dUTP. Clearly triphosphates are desirable for studies involving polymerase incorporation. However, diphosphates find utility in the study of certain phosphodieaterases such as that contained in the venom of the Eastern diamondback rattlesnake Crotalus adamanteous. Likewise, dinucleobase tetraphosphates are the substrate for a class of enzymes known as Fragile HIstidine Triad phosphatases or FHITs. Molecules of the current invention that contain four phosphates could be used to study the activity of FHITs in real-time.

Several phosphate modifications are know to be resistant to exonucleolytic degradation including phosphorothioate, phosphoramidate, alkyl-phosphonates, and boranophosphates. These modifications could also be incorporated into the molecules of the present invention either to block exonucleolytic degradation or to serve as a negative control for enzymes known not to act upon them.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include but are not limited to cyclopropyl, cyclobutyl, cyclopentyl, cyclohexyl, decahydronaphthalene, adamantane, indanyl, indenyl, fluorophorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "halogen" refers chlorine, fluorine, bromine or iodine. The term "halo" represents chloro, fluoro, bromo or iodo.

The term "optionally substituted" is intended to include both substituted and unsubstituted. Exemplary substituents include a halogen, lower alkyl, OH, $NO_2$, CN, $CO_2H$, O-lower alkyl, -aryl, -aryl-lower alkyl, $CO_2CH_3$, $CONH_2$, $OCH_2$, $CONH_2$, $NH_2$, $SO_2NH_2$, haloalkyl, O-haloalkyl, and the like. Thus, for example, an optionally substituted aryl can be represented by a pentafluorophenyl or a phenyl ring.

The terms "comprising" and "including" are used in an open, non-limiting sense.

It is understood that while a molecule of formula (1) may exhibit the phenomenon of tautomerism, the formula drawings within this specification expressly depict only one of the possible tautomeric forms. It is therefore to be understood that within the invention the formulae are intended to represent any tautomeric form of the depicted molecule and is not to be limited merely to a specific tautomeric form depicted by the formula drawings.

For example, the molecules of formula (1) contain one or more asymmetric centers and may thus give rise to diastereomers and optical isomers. The present invention includes all such possible diastereomers as well as their racemic mixtures, their substantially pure resolved enantiomers, all possible geometric isomers, and acceptable salts thereof. The above formula (1) is shown without a definitive stereochemistry at certain positions. The present invention includes all stereoisomers of formula (1) and acceptable salts thereof. Further, mixtures of stereoisomers as well as isolated specific stereoisomers are also included. During the course of the synthetic procedures used to prepare such molecules, or in using racemization or epimerization procedures known to those skilled in the art, the products of such procedures can be a mixture of stereoisomers.

The molecules of the present invention find utility in monitoring the progress of nucleic acid amplification reactions in real-time. As used herein, the term "nucleic acid amplification" refers to the process of making multiple copies of a single nucleic acid amplicon. Primer extension reactions and reactions in which a strand complementary to the template strand is synthesized but additional copies of the template strand are not generated, such as those described in U.S. Pat. No. 6,232,075, are not considered to be amplification reactions.

The molecules of the present invention find further utility in detecting the presence of active polymerase in a sample. The molecules of the present invention are effective reporters of polymerase activity because they do not function as a label until such time as they have been utilized as a substrate by a polymerase. They conditionally emit a measurable signal where said condition is usually utilization by a polymerase. Because they are "invisible" to the detection system until they are used by a polymerase, they can contaminate subsequent hybridization reactions without contributing to a background signal. The same cannot be said for fluorescently labeled nucleobases in which no quencher is present because they are continuously fluorescent and must be removed from a labeling reaction otherwise they will cause a significant background fluorescence signal.

The molecules of the present invention will find great utility in applications where it is desirable to label nucleic acids with indicators. Such applications include Southern blots, northern blots, in situ hybridization, and microarray hybridizations. In each of these applications, the failure to remove unincorporated label can lead to unacceptably high background signals. In an effort to reduce this background, investigators apply any one of a number of techniques known to those of reasonable skill in the art to remove said unincorporated labels. The molecule of the present invention do not require such post-labeling purification protocols. As a result, the labeled nucleic acid of interest can be applied in the downstream application without subsequent purification. The costs incurred with the purification step and fluid handling steps that might be required to automate it are obviated. Post-labeling purification remains a significant obstacle to full automation of molecular genotyping tests in clinical laboratories.

In a number of infectious diseases, one can determine the presence or absence of an infection by performing an assay for the presence of the infectious agent's DNA or RNA polymerase. In most cases where this approach is used, the test of choice is an enzyme linked immuno-absorbent assay or ELISA. The molecules of the present invention can be used as a safe, cost-effective and portable mechanism for detecting the presence or absence of a particular infectious agent.

Viral enzyme activity can currently be detected by performing an radiometric enzyme incorporation assay. In this type of assay, the sample is supplied with an [α-32P] dNTP which is incorporated by the polymerase (methods in enzymology). After a predetermined amount of time, the unincorporated nucleotide is separated from the incorporated nucleotide and the amount of the latter is quantified. This assay, while capable of measuring the presence of HIV reverse transcriptase is complicated by a number of obstacles including the removal of unincorporated nucleotides and the requirement for a scintillation counter.

The molecules of the present invention could be used in a similar assay however, one need not remove the unincorporated label. For example, the molecules of the present invention may be used to detect the presence of Human Immunodeficiency Virus (HIV) reverse transcriptase in a culture medium or serum sample. Further, this assay could be of tremendous utility in remote areas in which it is impractical to relocate scintillation counters. The molecules of the present invention could be added to a biological fluid of interest. The presence of a fluorescence emission above some threshold would indicate the presence of the viral polymerase. It is unlikely that human polymerases will be a confounding factor as they are much more discriminatory with respect to the nature of the nucleobase substitutions that will tolerate (17). In fact, polymerase selectivity may be conferred by the gamma-phosphate modification. The molecules of the present invention could also be used to monitor viral or bacterial replication in living cells.

DNA sequencing is an important component of any molecular biologist's repertoire. The molecules of the present invention may be useful in a number of DNA sequencing approaches by virtue of the fact that the unincorporated molecule does not contribute to background fluorescence.

The molecules of the present invention may be comprise part of a homogeneous or heterogeneous assay. As used herein, the term "homogenous" assay refers to an assay method wherein all the components are in the same phase (i.e., in solution). Likewise, the term "heterogeneous" assay refers to an assay method wherein at least one of the reactants in the assay mixture is attached to a solid phase, such as a solid support. The methods and reagents described herein make no distinction between heterogeneous and homogeneous assays. The molecules described herein can be adapted to either purpose.

The following examples illustrate aspects of the invention but in no way are intended to limit the scope of the present invention

EXAMPLES

Example 1

Synthesis of Fluorophorescein-dUTP-dabcyl

Figure 2:
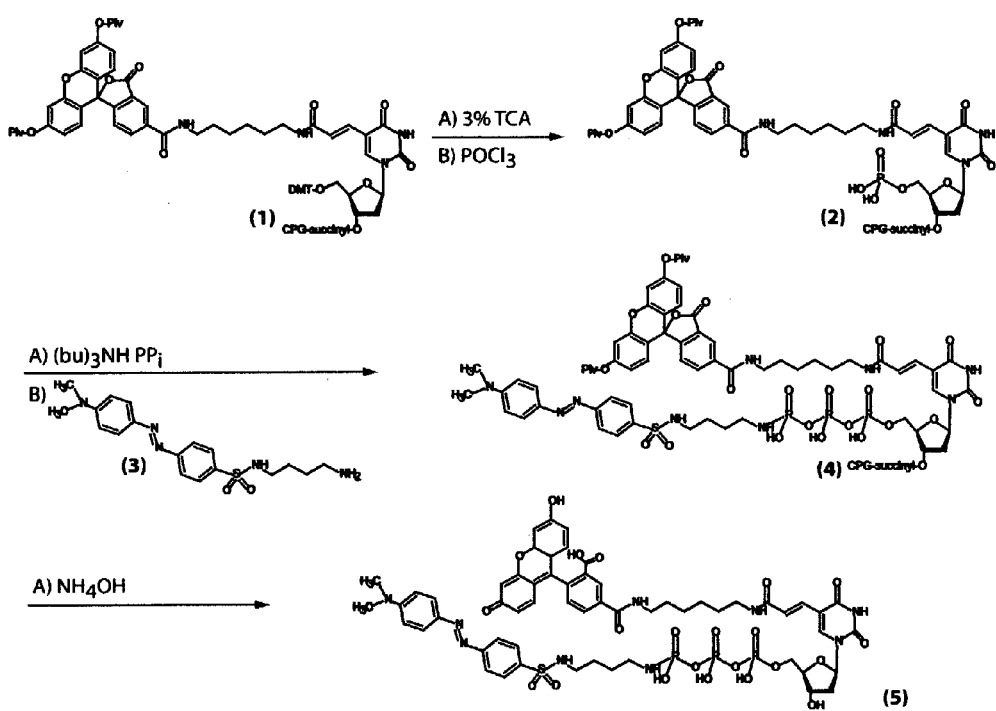
FIG. 2 shows the synthetic approach used to prepare one of the molecules of the present invention.

As shown in FIG. 2, 60.7 mg of Fluorescein-dT CPG was washed with anhydrous acetonitrile. The CPG was capped with cap mix A (Tetrahydrofuran/Lutidine/Acetic Anhydride (8:1:1)) and cap mix B (10% Methylimidazole in Tetrahydrofuran) in a 1:1 ratio for 30 minutes at room temperature then washed with anhydrous acetonitrile. The CPG was detritylated with a 3% trichloroacetic acid in dichloromethane then rinsed and washed with anhydrous acetonitrile. The reaction was neutralized with acetonitrile/pyridine (1:1), washed with acetonitrile and purged with Argon.

The CPG was washed with triethylphosphate and reacted with 1.0 ml of 1 M phosphorous oxychloride in triethylphosphate:trioctylamine (9:1) for 20 minutes. The CPG was once again washed with triethylphosphate. A mixture of 0.1 g/ml tributylammonium pyrophosphate in triethylphosphate and tributylamine (9:1) was added to the CPG and allowed to react for 20 minutes. A wash with triethylphosphate followed and the reaction was purged with Argon.

11.9 mg of dabsylamine (3) in trifluoroethanol/diisopropylethylamine (4:1) was added and the reaction was stirred at room temperature for 30 minutes. The CPG was washed with trifluoroethanol then with acetonitrile. The reaction was then purged with Argon.

Concentrated ammonium hydroxide was added and allowed to react for 30 minutes. The reaction mixture was filtered. The filtered material was treated again with concentrated ammonium hydroxide for 30 minutes and filtered. The filtered solutions were pooled and evaporated to dryness. The product was purified via reversed-phase HPLC. The peak of interest was detected with a prostar 320 UV/VIS detector and subject to further characterization. 4.1% overall yield.

Calculated mass 1351.1 M+1 1352.1. A 202 MHz $^{31}$P-NMR was obtained using an 85% $H_3PO_4$ standard (0 ppm). Resonances were observed at −0.06, −10.5 and −21.03 ppm, which correspond to the gamma, alpha and beta phosphates respectively. The resonances at −0.06 and −10.5 were appropriately split into doublets. The resonance at −21.03 was a triplet with a peak ratio of 1:2:1. Resonance integrals confirm that the α, β and γ phosphates were present at the predicted 1:1:1 ratio.

Example 2

Dabsyl-diaminobutane (3) Synthesis 1,4-diaminobutane was dissolved in acetonitrile. Dabsyl sulfonyl chloride was slurred in acetonitrile. The Dabsyl sulfonyl chloride slurry was added to the diaminobutane solution and reacted for 15 minutes. The reaction was quenched with water, diluted to 40% water and filtered. The filtrate was diluted to 60% water and re-filtered. The resulting filter cake was dried under high vacuum. The dry filter cake was dissolved in acetonitrile and dried in a rotoevaporator. The dried material was subject to further characterization. Calculated mass 375.49. Observed m+1 376.3. Elemental analysis—Calculated: % C, 57.57; % H, 6.71; % N, 18.65. Observed: % C, 57.48; % H, 6.35; % N, 18.33.

Figure 3:
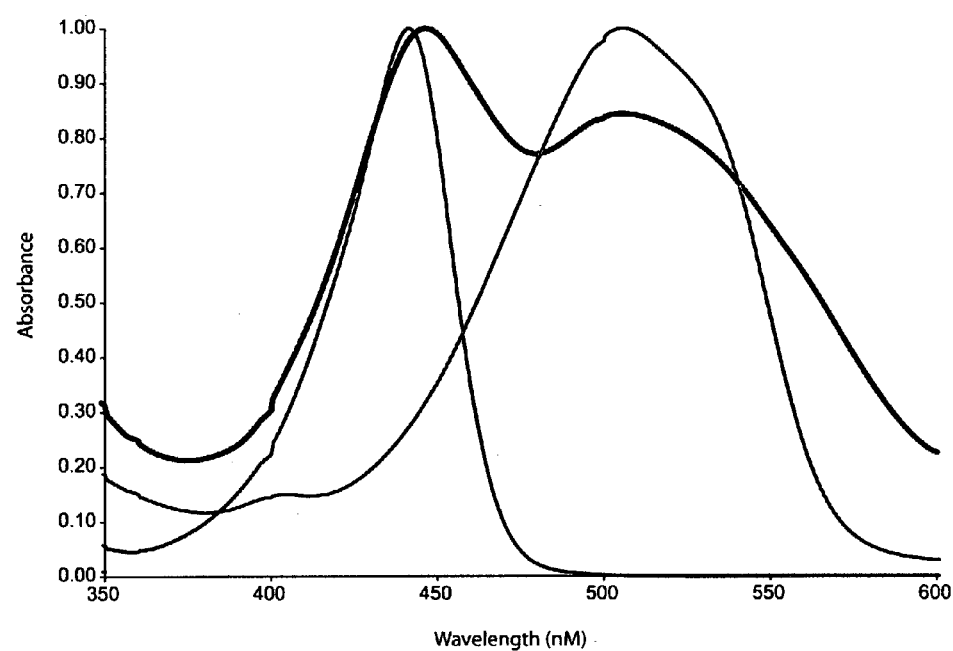
FIG. 3 shows the absorption spectrum of one of the molecules of the present invention and some controls.

Optical Absorbance Properties:

As shown in FIG. 3, the UV-visible absorbance spectrum indicates a strong absorbance at 260 nm, consistent with the presence of the uridine nucleobase (not shown). Additional peaks were observed at 440 nm and 520 nm, corresponding to the fluorescein and dabsyl moieties respectively. Fluorescein-dUTP is shown in red, dUTP-dabsylaminobutane is shown in blue and the molecule of the present invention is shown in black. All spectra were normalized to the highest peak within the window shown to facilitate comparison (517 nm for fluorescein-dUTP, 444 nm for dUTP-dabsylaminobutane and 448 nm for fluorescein-dUTP-dabsylaminobutane).

Figure 4A:
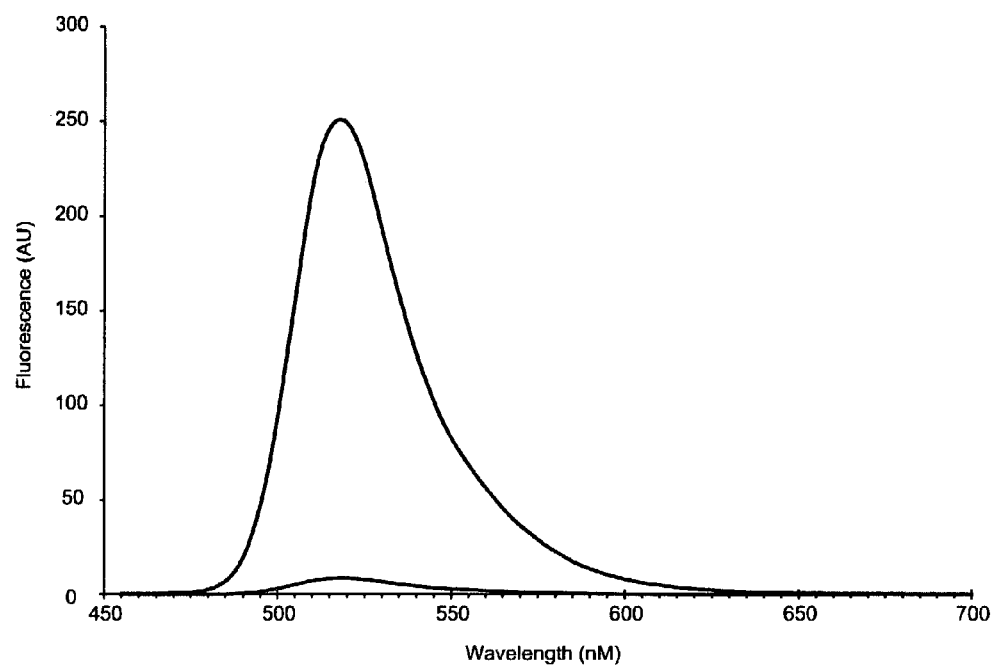
FIG. 4A shows the fluorescence emission spectrum of a molecule of the present invention in the presence and absence of a quencher moiety.

Fluorescence Properties:

A fluorescence emission spectrum for fluorescein-dUTP-dabsylaminobutane is shown in the FIG. 4A (top panel). Fluorescein emission is near-quantitatively quenched (>98%) as compared to a fluorescein-dUTP control. Fluorescein-dUTP is roughly 400 times more fluorescent than fluorescein-dUTP-dabsylaminobutane.

Hydrolysis if the IQN triphosphate backbone should result in an increase in fluorescence, as the dabcyl moiety will no longer be in sufficient proximity to quench fluorescein emission. Two different approaches were used to demonstrate this. In the first approach, the fluorescein-dUTP-dabsylaminobutane is heated under alkaline conditions (pH>13) known to hydrolyze nucleotides. A time dependent increase in fluorescence emission centered at 520 nm was observed (fluorescein has an emission maximum at 520 nm). No increase in fluorescence is observed when the fluorescein-dUTP-dabsylaminobutane is heated under neutral conditions.

Figure 4B:
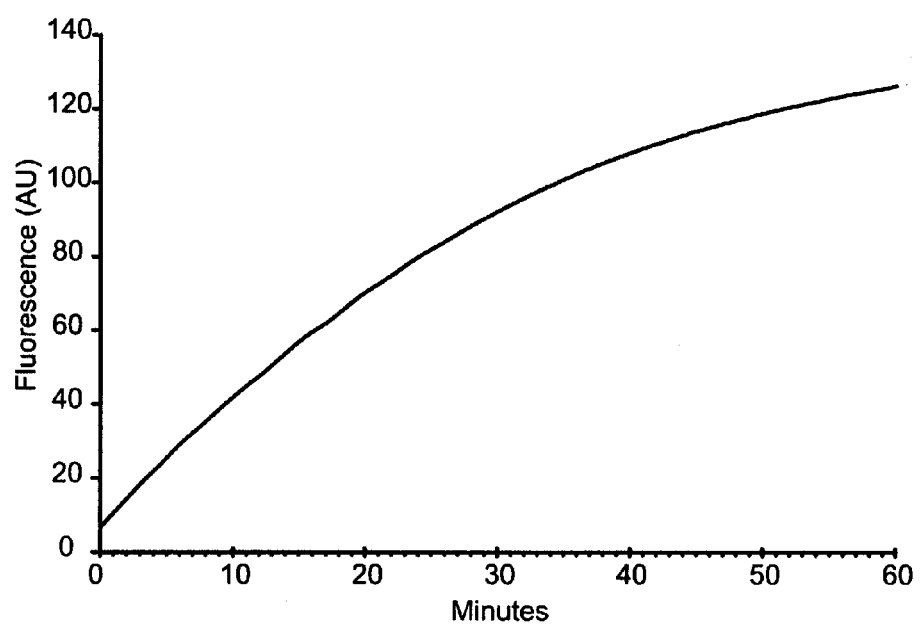
FIG. 4B shows the change in fluorescence intensity that results when molecules of the present invention are incubated with snake venom phosphodiesterase.

Fluorescein-dUTP-dabsylaminobutane was treated with snake venom phosphodiesterase (SVP) an enzyme that readily cleaves oligo- and mononucleosides to nucleoside monophosphates. The conditions under which this reaction was performed more closely mimic those that might be observed in a mesophilic polymerization reaction. As shown in the accompanying figure, SVP rapidly hydrolyzes fluorescein-dUTP-dabsylaminobutane with a concomitant increase in fluorescence intensity at 520 nm (FIG. 4B)

Figure 5:
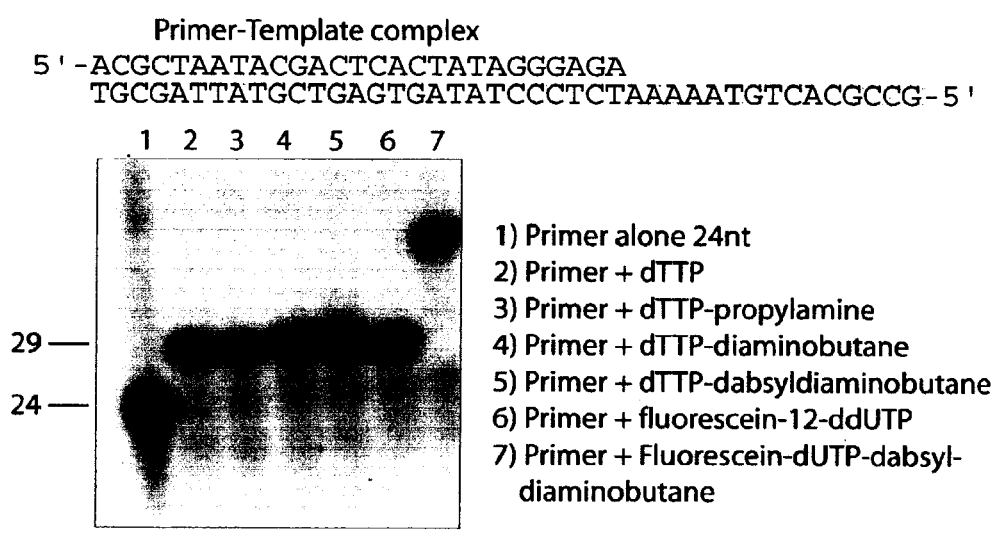
FIG. 5 shows that molecules of the present invention are substrates of Avian Myeloblastosis Virus Reverse Transcriptase.

Substrate Properties:

An oligonucleotide primer extension assay was performed using Avian Myeloblastosis Virus (AMV) reverse transcriptase (RT) and fluorescein-dUTP-dabsylaminobutane (described above) (FIG. 5). The primer-template complex shown was extended by AMV RT in the presence of dTTP or the indicated analog. Nucleotide positions are shown on the left. Note that primers containing a fluorescein-dU or fluorescein-ddU residue migrate aberrantly. The bands were resolved on a 20% polyacrylamide, urea gel which was stained to highlight their location. The band in lane 7 represents the addition of 5 consecutive fluorescein-dU residues to the primer.

REFERENCES CITED

1. Various, *Nat Genet* 21, 1–60 (January, 1999).
2. Various, *Nat Genet* 32 Suppl, 461–552 (December, 2002).
3. N. P. Shah et al., *Cancer Cell* 2, 117–25 (August, 2002).
4. M. E. Gorre et al., *Science* 293, 876–80 (Aug. 3, 2001).
5. K. Nath, J. W. Sarosy, J. Hahn, C. J. Di Como, *J Biochem Biophys Methods* 42, 15–29 (Jan. 3, 2000).
6. I. V. Kutyavin et al., *Nucleic Acids Res* 28, 655–61 (Jan. 15, 2000).
7. V. Lyamichev, M. A. Brow, J. E. Dahlberg, *Science* 260, 778–83 (May 7, 1993).
8. J. Compton, *Nature* 350, 91–2 (Mar. 7, 1991).
9. E. Fahy, D. Y. Kwoh, T. R. Gingeras, *PCR Methods Appl* 1, 25–33 (August, 1991).
10. P. M. Lizardi et al., *Nat Genet* 19, 225–32 (July, 1998).
11. M. Jett et al., *Proceedings of NATO Conference: Operational Issues in Chemical and Biological Defense Human Factors in Medicine Panel* (In Press, 2001).
12. P. Wu, L. Brand, *Anal Biochem* 218, 1–13 (April, 1994).
13. G. Benga, S. J. Strach, *Biochim Biophys Acta* 400, 69–79 (Jul. 21, 1975).
14. H. Weizman, Y. Tor, *J Am Chem Soc* 124, 1568–9 (Feb. 27, 2002).
15. J. A. Secrist, 3rd, J. R. Barrio, N. J. Leonard, *Science* 175, 646–7 (Feb. 11, 1972).
16. W. R. McClure, K. H. Scheit, *FEBS Lett* 32, 267–9 (Jun. 1, 1973).
17. A. A. Arzumanov, D. G. Semizarov, L. S. Victorova, N. B. Dyatkina, A. A. Krayevsky, *J Biol Chem* 271, 24389–94 (Oct. 4, 1996).

The disclosure of each publication, patent or patent application mentioned in this specification is specifically incorporated by reference herein in its entirety.

The invention has been illustrated by reference to specific examples and preferred embodiments. However, it should be understood that the invention is intended not to be limited by the foregoing description, but to be defined by the appended claims and their equivalents

What is claimed is:

1. A molecule comprising the formula (1) shown below

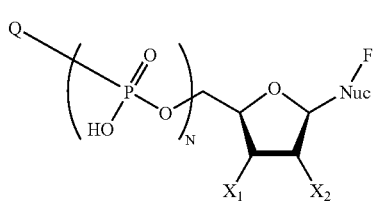

(1)

wherein:

Nuc represents a nucleobase selected from the group consisting of adenine, cytosine, guanine, thymidine, uracil and analogs thereof;

N represents a number from 1 through 8 indicating the number of phosphate moieties present in said molecule;

$X_1$ and $X_2$ are independently selected from the group H, OH, $NH_2$, O-alkyl, N-alkyl, S-Alkyl, P-alkyl, a halogen, an alkyl, a cyclo-alkyl, and an aromatic containing group, wherein the alkyl and cycloalkyl possess varying degrees of unsaturation and are optionally substituted; and F and Q comprise a pair of indicators, wherein cleavage of the molecule results in separation of the indicators which, in turn, yields a change in a measurable signal, further wherein F is not a quencher of Q's fluoresence.

2. The molecule according to claim 1, wherein said measurable signal is selected from fluorescence, magnetic field, and radiation intensity.

3. The molecule according to claim 1, wherein said F and Q are selected from the group consisting of fluorophores, quenchers, shift reagents, spin labels, radioisotopes, and magnetic reasonance contrast agents.

4. The molecule according to claim 1, wherein said F and Nuc cyclize to form an intrinsically fluorescent nucleobase analog.

5. The molecule according to claim 1 wherein F is bound to Nuc by a cleavable linker.

6. The molecule according to claim 1, wherein the sugar shown in formula (1) is selected from the group consisting of optionally substituted riboses, deoxyriboses, acyclics, carbocyclics, dideoxyriboses, hexoses, and dideoxydidehydroriboses.

7. The molecule according to claim 1, wherein F is a fluorophore and Q is a quenching moiety and said change in measurable signal comprises a change in fluorescence intensity, lifetime or polarization.

8. The molecule according to claim 6, wherein said fluorophore is selected from the group consisting of optionally substituted pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins (FAM), 5-(2'-aminoethyl) aminonapthalene-1-sulfonic acids (EDANS), anthranilamides, terbium chelates, Reactive Red 4, Texas reds, and BODIPY dyes.

9. The molecule according to claim 7, wherein said quenching moiety is selected from the group consisting of optionally substituted phenyls, naphthyls, anthracenyls, benzothiazoles, benzoxazoles, or benzimidazoles, pyrenes, anthracenes, naphthalenes, acridines, stilbenes, indoles, benzindoles, oxazoles, benzoxazoles, thiazoles, benzothiazoles, 4-amino-7-nitrobenz-2-oxa-1,3-diazoles, cyanines, carbocyanines, carbostyryls, porphyrins, salicylates, anthranilates, azulenes, perylenes, pyridines, quinolines, coumarins, polyazaindacenes, xanthenes, oxazines, benzoxazines, carbazines, phenalenones, benzphenalenones, carbazines, oxazines, 4-bora-3a,4a-diaza-s-indacenes, fluorophoresceins, rhodamines, rhodols, 5-carboxyfluorophoresceins (FAM), 5-(2'-aminoethyl) aminonapthalene-1-sulfonic acids (EDANS), anthranilamides, terbium chelates, Reactive Red 4, dabcyls, dabsyls, nitrotyrosines, malachite greens, Texas reds, dinitrobenzenes, and BODIPY dyes.

10. The molecule according to claim 1, wherein one or more of said phosphates of the molecule of formula (1) are replaced with phosphorothioate, phosphoramidate, phosphonate, or alkyl-phosphonate.

11. A method of detecting nucleic acid amplification comprising the steps of:

(a) contacting a polymerase with a primer, a template, nucleobase triphosphates and one or more molecules of the formula (1) shown below in a medium in which said polymerase is active:

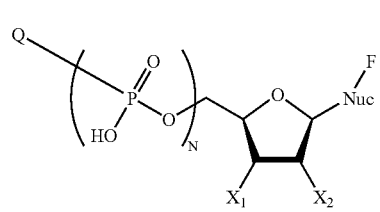

(1)

wherein:

Nuc represents a nucleobase selected from the group consisting of adenine, cytosine, guanine, thymidine, uracil and analogs thereof;

N represents a number from 1 through 8 indicating the number of phosphate moieties present in said molecule;

$X_1$ and $X_2$ are independently selected from the group H, OH, $NH_2$, O-alkyl, N-alkyl, S-Alkyl, P-alkyl, a halogen, an alkyl, a cyclo-alkyl, and an aromatic containing group, wherein the alkyl and cycloalkyl possess varying degrees of unsaturation and are optionally substituted; and F and Q comprise a pair of indicators, wherein cleavage of the molecule results in separation of the indicators which, in turn, yields a change in a measurable signal; and (b) detecting a change a measurable signal.

12. The method according to claim 11, wherein said nucleic acid amplification process is selected from PCR, RCA, NASBA, 3SR.

13. A method of detecting a polymerase comprising the steps of:

(a) contacting said polymerase with a primer, a template, nucleobase triphosphates and one or more molecules of the formula (1) shown below in a medium in which said polymerase is active:

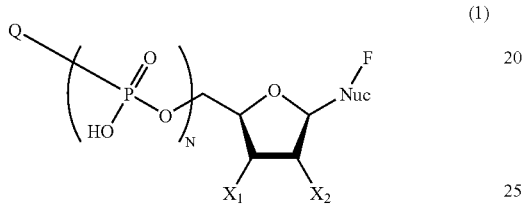

(1)

wherein:

Nuc represents a nucleobase selected from the group consisting of adenine, cytosine, guanine, thymidine, uracil and analogs thereof;

N represents a number from 1 through 8 indicating the number of phosphate moieties present in said molecule;

$X_1$ and $X_2$ are independently selected from the group H, OH, $NH_2$, O-alkyl, N-alkyl, S-Alkyl, P-alkyl, a halogen, an alkyl, a cyclo-alkyl, and an aromatic containing group, wherein the alkyl and cycloalkyl possess varying degrees of unsaturation and are optionally substituted; and F and Q comprise a pair of indicators, wherein cleavage of the molecule results in separation of the indicators which, in turn, yields a change in a measurable signal; and (b) detecting a change said measurable signal.

14. The method according to claim 13, wherein said polymerase is a DNA polymerase, an RNA polymerase or a reverse transcriptase.

15. The method according to claim 13, wherein polymerase is contained within virus particle.

16. The method according to claim 15, wherein said virus particle is an HIV particle and said method allows for the real time detection of the presence of HIV reverse transcriptase in a sample.

17. The method according to claim 13, wherein said medium is a body fluid selected from blood, plasma, serum, CSF, urine, semen, tears, saliva, bile, gastric secretions and breast milk.

18. A method of detecting a phosphodiesterase comprising the steps of:

(a) contacting one and one or more molecules of the formula (1) shown below with a phosphodiesterase in a medium in which said phosphodiesterase is enzymatically active:

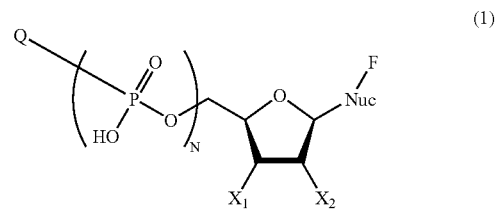

(1)

wherein:

Nuc represents a nucleobase selected from the group consisting of adenine, cytosine, guanine, thymidine, uracil and analogs thereof;

N represents a number from 1 through 8 indicating the number of phosphate moieties present in said molecule;

$X_1$ and $X_2$ are independently selected from the group H, OH, $NH_2$, O-alkyl, N-alkyl, S-Alkyl, P-alkyl, a halogen, an alkyl, a cyclo-alkyl, and an aromatic containing group, wherein the alkyl and cycloalkyl possess varying degrees of unsaturation and are optionally substituted; and F and Q comprise a pair of indicators, wherein cleavage of the molecule results in separation of the indicators which, in turn, yields a change in a measurable signal; and (b) detecting a change in said measurable signal.

19. A method of detecting nucleobase cyclase activity comprising the steps of:

(a) contacting one or more molecules of the formula (1) shown below with said cyclase in a medium in which said cyclase is enzymatically active

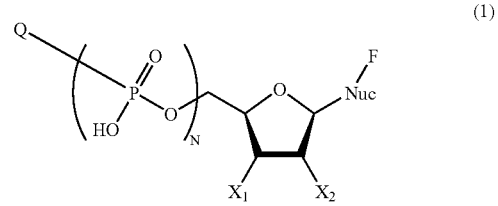

(1)

wherein:

Nuc represents a nucleobase selected from the group consisting of adenine, cytosine, guanine, thymidine, uracil and analogs thereof;

N represents a number from 1 through 8 indicating the number of phosphate moieties present in said molecule;

$X_1$ and $X_2$ are independently selected from the group H, OH, $NH_2$, O-alkyl, N-alkyl, S-Alkyl, P-alkyl, a halogen, an alkyl, a cyclo-alkyl, and an aromatic containing group, wherein the alkyl and cycloalkyl possess varying degrees of unsaturation and are optionally substituted; and F and Q comprise a pair of indicators, wherein cleavage of the molecule results in separation of the indicators which, in turn, yields a change in a measurable signal; and (b) detecting a change in said measurable signal.

20. An assay for detecting the presence of an active viral polymerase in a sample comprising the following components: a polymerase with a primer, a template, nucleobase triphosphates and one or more molecules of the formula (1) shown below:

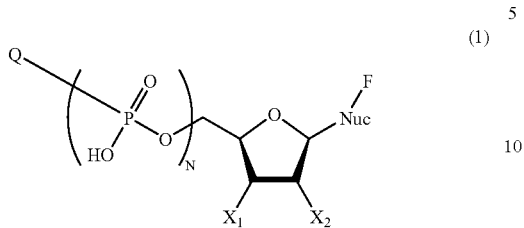

(1)

wherein:

Nuc represents a nucleobase selected from the group consisting of adenine, cytosine, guanine, thymidine, uracil and analogs thereof;

N represents a number from 1 through 8 indicating the number of phosphate moieties present in said molecule;

$X_1$ and $X_2$ are independently selected from the group H, OH, $NH_2$, O-alkyl, N-alkyl, S-Alkyl, P-alkyl, a halogen, an alkyl a cyclo-alkyl, and an aromatic containing group, wherein the alkyl and cycloalkyl possess varying degrees of unsaturation and are optionally substituted; and F and Q comprise a pair of indicators, wherein cleavage of the molecule results in separation of the indicators which, in turn, yields a change in a measurable signal.

21. The assay of claim 20, wherein said sample comprises a body fluid selected from blood, plasma, serum, CSF, urine, semen, tears, saliva, bile, gastric secretions and breast milk.

22. The assay of claim 20, wherein the viral polymerase comprises HIV reverse transcriptase.

23. A method of labeling a nucleic acid comprising:
(a) contacting a polymerase with a primer, a nucleic acid template, nucleoside triphosphates and one or more compounds of the formula (1) shown below in a medium in which said polymerase is active:

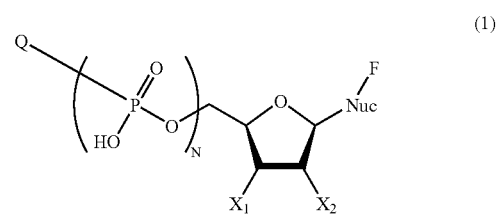

(1)

wherein:

Nuc represents a nucleobase selected from the group consisting of adenine, cytosine, guanine, thymidine, uracil and analogs thereof;

N represents a number from 1 through 8 indicating the number of phosphate moieties present in said molecule;

$X_1$ and $X_2$ are independently selected from the group H, OH, $NH_2$, O-alkyl, N-alkyl, S-Alkyl, P-alkyl, a halogen, an alkyl, a cyclo-alkyl, and an aromatic containing group, wherein the alkyl and cycloalkyl possess varying degrees of unsaturation and are optionally substituted; and F and Q comprise a pair of indicators, wherein cleavage of the molecule results in separation of the indicators which, in turn, yields a change in a measurable signal; and (b) allowing the one or more compounds of formula (1) to be cleaved and incorporated into a nucleic acid synthesized by said polymerase, thereby resulting in a labeled nucleic acid that emits a measurable signal.

24. The method according to claim 23, wherein said polymerase is a DNA polymerase, an RNA polymerase or a reverse transcriptase.

* * * * *

SEQUENCE LISTING

<160> NUMBER OF SEQ ID NOS: 2

<210> SEQ ID NO 1
<211> LENGTH: 27
<212> TYPE: DNA
<213> ORGANISM: artificial sequence
<220> FEATURE:
<223> OTHER INFORMATION: oligonucleotide primer

<400> SEQUENCE: 1
acgctaatac gactcactat agggaga                                27

<210> SEQ ID NO 2
<211> LENGTH: 42
<212> TYPE: DNA
<213> ORGANISM: artificial sequence
<220> FEATURE:
<223> OTHER INFORMATION: oligonucleotide template

```
<400> SEQUENCE: 2
tgcgattatg ctgagtgata tccctctaaa aatgtcacgc cg                           42
```